(12) United States Patent
Canty et al.

(10) Patent No.: US 11,327,064 B2
(45) Date of Patent: May 10, 2022

(54) FOAM/LIQUID MONITORING SYSTEM

(71) Applicant: J.M. Canty, Inc., Buffalo, NY (US)

(72) Inventors: Thomas Canty, Williamsville, NY (US); Michael Rizzo, Blasdell, NY (US); Meredith McDonald, Tonawanda, NY (US); Colleen Kelley, Williamsville, NY (US); Justin Halbach, Clarence, NY (US)

(73) Assignee: J.M. CANTY, INC., Buffalo, NY (US)

( * ) Notice: Subject to any disclaimer, the term of this patent is extended or adjusted under 35 U.S.C. 154(b) by 506 days.

(21) Appl. No.: 15/910,033

(22) Filed: Mar. 2, 2018

(65) Prior Publication Data

US 2018/0252692 A1 Sep. 6, 2018

Related U.S. Application Data

(60) Provisional application No. 62/466,420, filed on Mar. 3, 2017.

(51) Int. Cl.
*H04N 5/00* (2011.01)
*G01N 21/00* (2006.01)
*G01N 33/14* (2006.01)
*G01N 21/15* (2006.01)
*G01N 21/27* (2006.01)
(Continued)

(52) U.S. Cl.
CPC ............ *G01N 33/146* (2013.01); *B01J 3/004* (2013.01); *B01J 8/1809* (2013.01); *C12M 23/22* (2013.01); *C12M 41/02* (2013.01); *G01N 21/15* (2013.01); *G01N 21/272* (2013.01); *G06K 9/00771* (2013.01); *H04N 7/183* (2013.01); *B01J 2208/0061* (2013.01); *B01J 2219/00182* (2013.01); *G01N 2021/158* (2013.01);
(Continued)

(58) Field of Classification Search
CPC .............. B01J 8/1809; B01J 2208/0061; B01J 2219/00182; B01J 3/004; H04N 7/183; H04N 2005/2255; H04N 5/2252; C12M 23/22; C12M 41/02; G01N 33/146; G01N 21/15; G01N 21/272; G01N 2021/158; G01N 2201/062; G06K 9/00771
See application file for complete search history.

(56) References Cited

U.S. PATENT DOCUMENTS 6,450,655 B1 9/2002 Walck et al.
6,771,366 B2 * 8/2004 Canty .................... G01N 21/05
356/246
(Continued)

FOREIGN PATENT DOCUMENTS

DE 4028871 A1 3/1992
DE 102010012162 A1 9/2011

*Primary Examiner* — Zhihan Zhou
(74) *Attorney, Agent, or Firm* — Leydig, Voit & Mayer, Ltd.

(57) ABSTRACT

A monitoring system for monitoring a process includes a housing with a viewing panel. The viewing panel includes a view port. An emitter generates light and illuminates an observation zone of the process. A detector is disposed within the housing and is configured to detect light entering the housing through the view port and create a plurality of images of the process in the observation zone. A thermal regulation system is configured to generate heat in the vicinity of the viewing panel of the housing so as to increase the temperature of at least the view port above ambient temperature.

38 Claims, 13 Drawing Sheets

(51) Int. Cl.
*G06K 9/00* (2022.01)
*H04N 7/18* (2006.01)
*C12M 1/21* (2006.01)
*C12M 1/00* (2006.01)
*B01J 3/00* (2006.01)
*B01J 8/18* (2006.01)
*H04N 5/225* (2006.01)

(52) U.S. Cl.
CPC ..... *G01N 2201/062* (2013.01); *H04N 5/2252* (2013.01); *H04N 2005/2255* (2013.01)

(56) References Cited

U.S. PATENT DOCUMENTS

| | | | | |
|---|---|---|---|---|
| 2002/0134438 | A1* | 9/2002 | Vilagines | F16K 37/0058 137/559 |
| 2005/0059142 | A1* | 3/2005 | Vinarov | C12M 41/02 435/295.1 |
| 2009/0244910 | A1* | 10/2009 | Meng | F21V 23/0442 362/373 |
| 2012/0031453 | A1* | 2/2012 | Rao | F25B 21/02 136/242 |
| 2013/0039810 | A1* | 2/2013 | Riechers | C12M 41/02 422/82.05 |
| 2015/0072400 | A1* | 3/2015 | Clarke | C12M 21/02 435/257.1 |
| 2016/0166719 | A1* | 6/2016 | Pezzi | A61L 2/0023 607/105 |
| 2017/0003041 | A1* | 1/2017 | Kim | F24F 3/153 |
| 2017/0349874 | A1* | 12/2017 | Jaques | C12M 27/20 |
| 2018/0143143 | A1* | 5/2018 | Coetzee | G01N 21/9027 |

* cited by examiner

FOAM/LIQUID MONITORING SYSTEM

CROSS-REFERENCE TO RELATED APPLICATIONS

This application claims benefit of U.S. Provisional Patent Application No. 62/466,420, which was filed on Mar. 3, 2017.

FIELD OF THE DISCLOSURE

The present disclosure relates to imaging devices that monitor manufacturing processes.

BACKGROUND OF THE INVENTION

The system, devices, and methods under consideration relate to the monitoring and control of manufacturing processes. Due to the nature of some processes, such as those involving fermentation, foaming is a common occurrence. To control foaming, system operators routinely add anti-foam agents (e.g., food grade oils) to reduce the negative effects of foaming and prevent product from flowing out of manufacturing vessel outlets, which can plug filters and condensation units, thus causing production problems. In addition, limited or no viewing of the inside of the vessel may occur as a result of condensation, preventing the operator from being able to monitor the amount of foam inside the vessel and complicating the assessment of an appropriate amount of anti-foam to add. Therefore, the operator response can be subjective, which can lead to anti-foam overdosing since that is the least damaging response but is still detrimental to the process.

In some systems, capacitance probes are mounted in the top head of the manufacturing vessel, which are triggered when they detect a high foam level, which initiates an addition of anti-foam agents. A problem with such probes is they do not enable a continuous proportional response but are based on contact height without regard to how fast the foam is rising, which can either cause over-dosing of the anti-foam or an under response to the foam level. The amount of foam covering the surface, the size of the bubbles or color of the foam is useful information for determining when, and how much anti-foam ingredients should be added to stop a process or continue onto the next step. Accordingly, reliance on a subjective operator or foam probes could result in a potentially detrimental response.

SUMMARY OF THE DISCLOSURE

The devices and methods of the present disclosure may be used in fermenters or other processing vessels, tanks and centrifuges, and other containers, for example. The present device allows a user to view the inside of the vessel, and for example, determine when a vessel is empty and clean and allows a user to observe and determine aspects of a manufacturing process. In one aspect, the disclosure describes an integral camera and light combination with a thermal regulation system and optional process based level monitoring with a small footprint construction to allow it to be used in research and pilot plant vessels as well as full-scale production environments. The disclosure describes an improved viewing capability of processes by mounting a device in an optimum location of the vessel. In yet another aspect, the disclosure describes a device for viewing and imaging-based assessment and quantification of foam.

In one aspect, the disclosure describes a monitoring system for monitoring a process includes a housing with a viewing panel. The viewing panel includes a view port. An emitter generates light and illuminates an observation zone of the process. A detector is disposed within the housing and is configured to detect light entering the housing through the view port and create a plurality of images of the process in the observation zone. A thermal regulation system is configured to generate heat in the vicinity of the viewing panel of the housing so as to increase the temperature of at least the view port above ambient temperature.

In a separate aspect, the disclosure describes a bubble trap and monitoring system including a bubble trap housing. The bubble trap housing includes a base section at a first end and an expanded section, wherein the expanded section has a wider diameter than the base section, and wherein the base section is attached to the expanded section by a tapered section. An automated gas bleed valve is attached to the housing in fluid communication with the expanded section for venting gas therefrom. A monitoring system for monitoring a process is attached to the bubble trap housing, including a housing including a viewing panel. The viewing panel includes a view port. An emitter is configured to generate light and illuminate an observation zone of the process. A detector is disposed within the housing and is configured to detect light entering the housing through the view port and create a plurality of images of the process in the observation zone. A thermal regulation system is configured to generate heat in the vicinity of the viewing panel of the housing so as to increase the temperature of at least the view port above ambient temperature.

Yet another aspect is directed to a method of maintaining the level of fluid within a bubble trap, which bubble trap includes a bubble trap housing; a gas bleed valve attached to the housing and in fluid communication with the bubble trap housing for venting gas therefrom; and a monitoring system for monitoring a process. The monitoring system includes a housing including a viewing panel. The viewing panel includes a view port. An emitter is configured to generate light and illuminate an observation zone of the process. A detector is disposed within the housing and is configured to detect light entering the housing through the view port and create a plurality of images of the process in the observation zone. A thermal regulation system is configured to generate heat in the vicinity of the viewing panel of the housing so as to increase the temperature of at least the view port above ambient temperature, wherein the method includes monitoring the level of the fluid by imaging an observation zone of the bubble trap with the monitoring system; determining when the level of the fluid drops below a selected level; opening the gas bleed valve to vent gas until the fluid level is restored to above the selected level, and closing the gas bleed valve.

DETAILED DESCRIPTION

Figure 1:
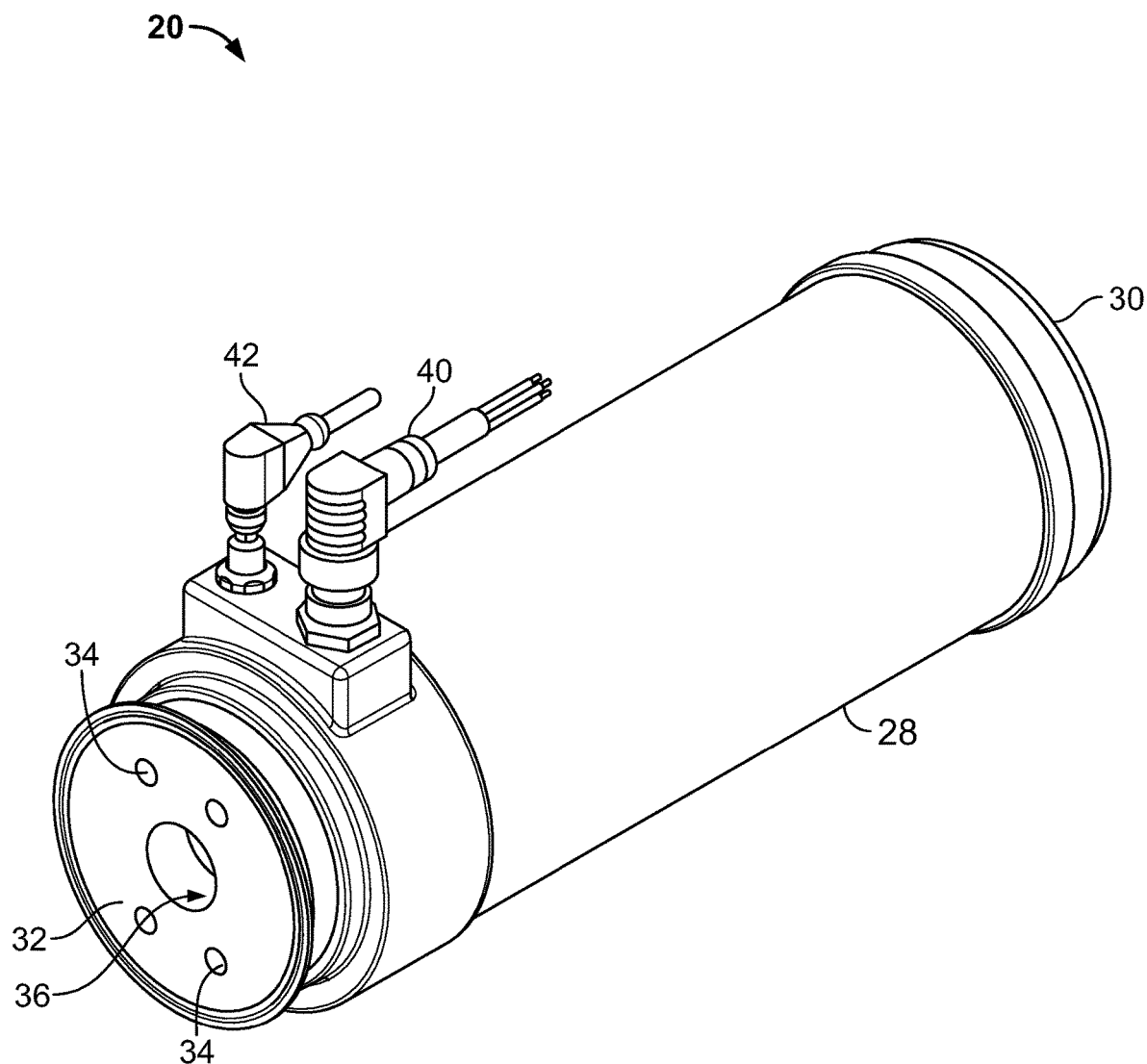
FIG. 1 is a front perspective view of a monitoring device according to an embodiment of the disclosure.
Figure 2:
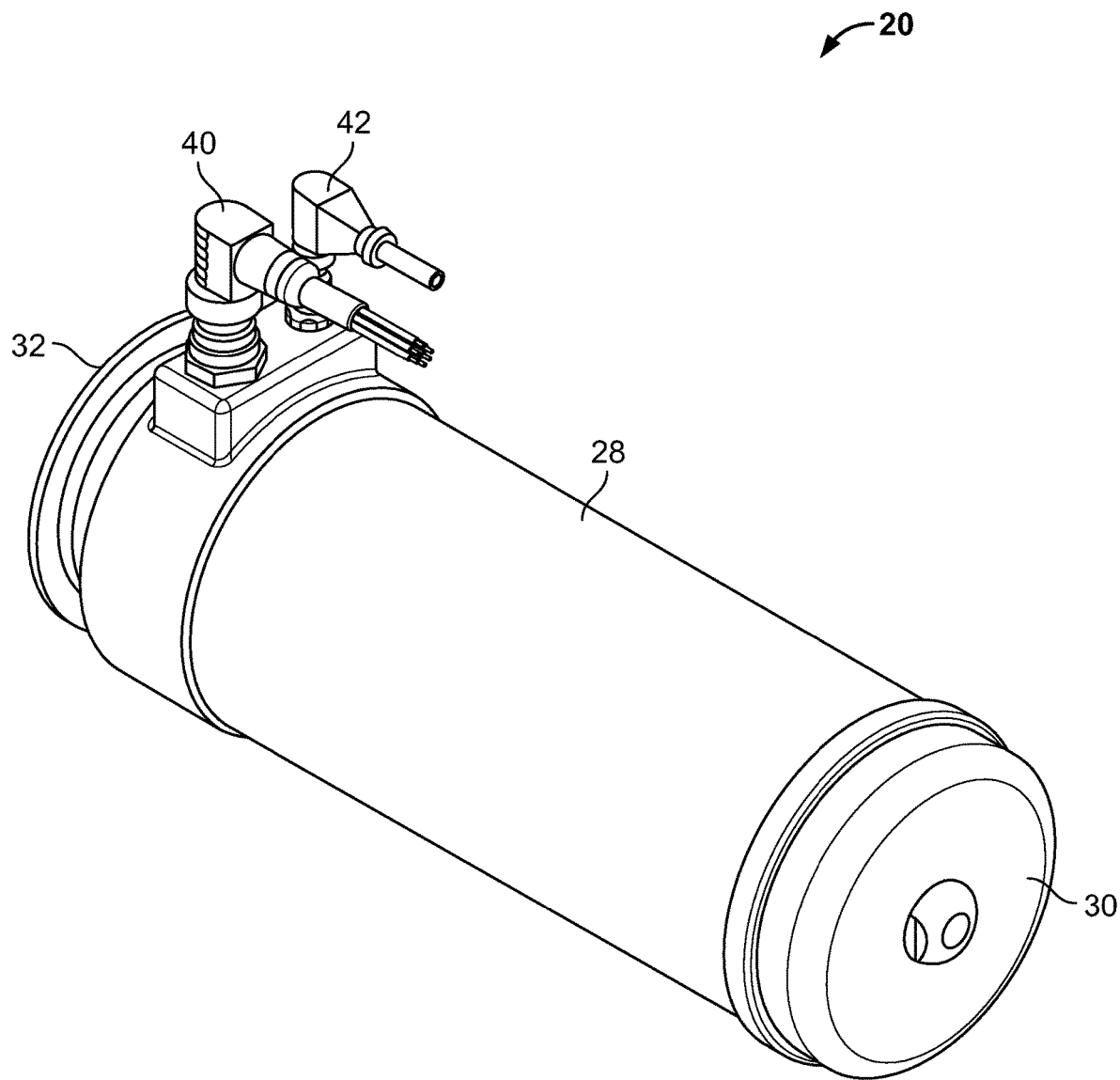
FIG. 2 is a rear perspective view of the monitoring device of FIG. 1.
Figure 3:
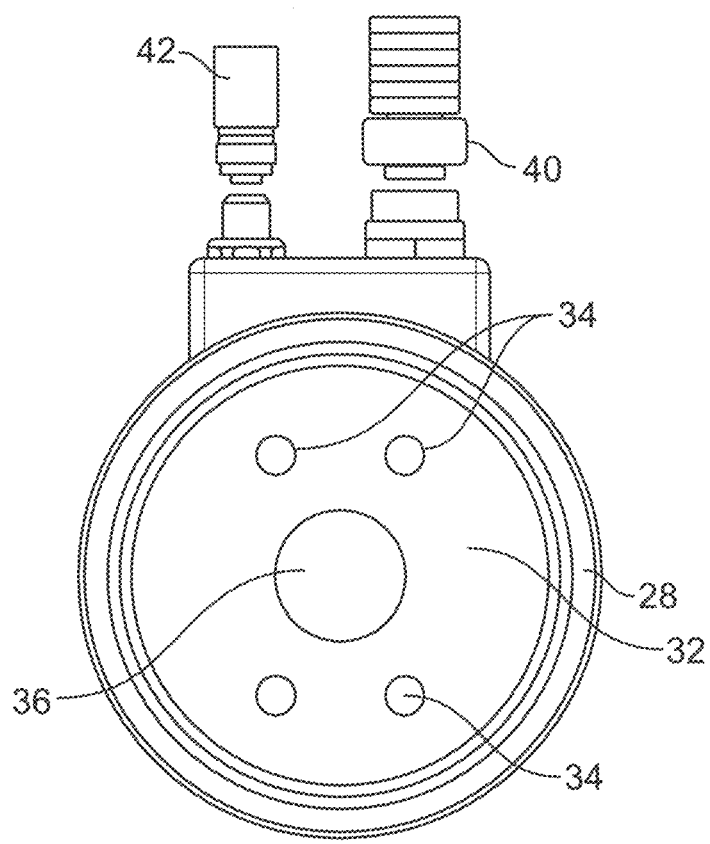
FIG. 3 is a front view of the monitoring device of FIG. 1.
Figure 4:
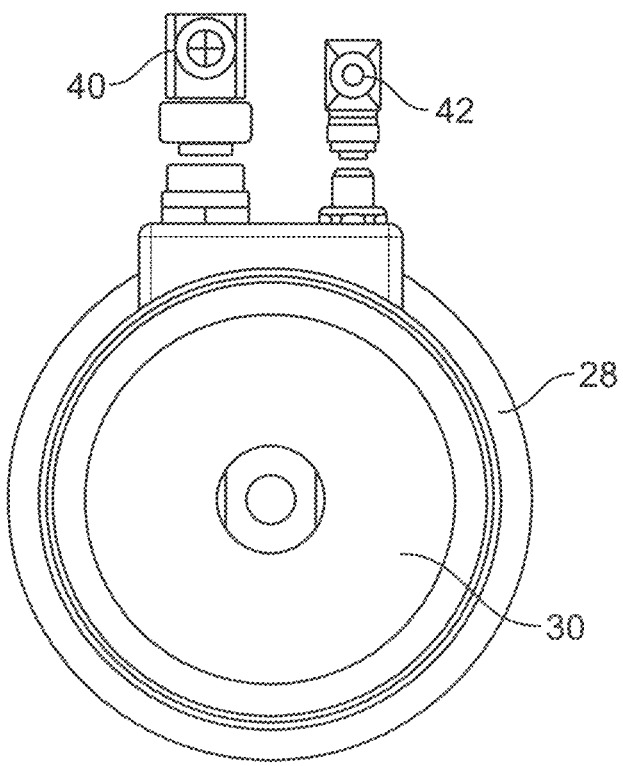
FIG. 4 is a rear view of the monitoring device of FIG. 1
Figure 5:
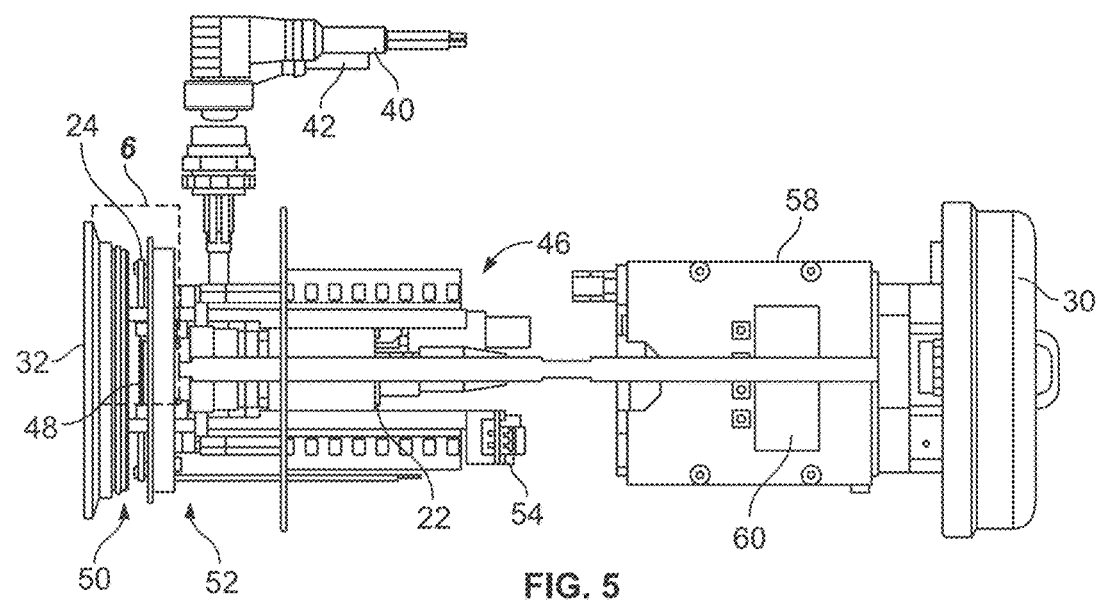
FIG. 5 is a side view of the monitoring device of FIG. 1 with a housing part removed.
Figure 6:
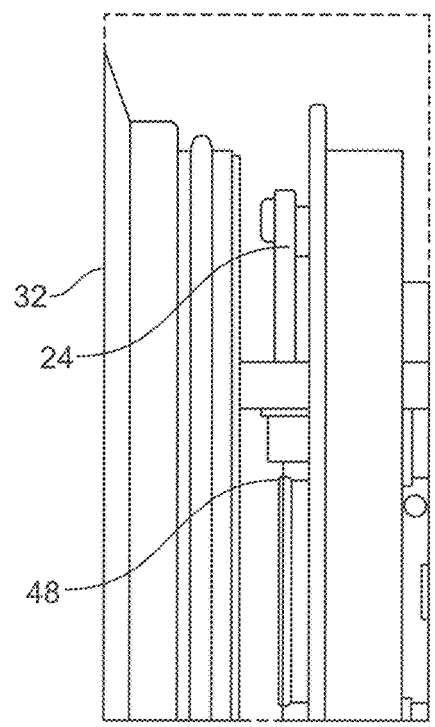
FIG. 6 is a partial, close up view of the front portion of the monitoring device of FIG. 5.

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims. The terms configured and configuration as used herein refer to specific structural sizes and shapes.

The device of the disclosure includes a detector and emitter combination with an integrated thermal regulation system to reduce or prevent condensation to enable unobstructed viewing into process vessels (fermenters, or vessels that contain surfactants, processes that include or cause the generation of foam, etc.) as well as optional incorporation of analysis of the manufacturing process to help optimize manufacturing.

Reference is made to FIGS. 1-6, which generally illustrates a monitoring device 20 with a reduced footprint that includes a detector 22 and an emitter 24 enclosed in one housing 28. The present monitoring device 20 may include the multi-port illuminating and viewing unit (see U.S. Pat. No. 6,450,655, incorporated herein in its entirety) or aspects thereof.

The housing 28 may be any suitable shape, such as a hollow canister, with suitable supports and fixtures as is known in the art for mounting the housing and internal elements and made of any suitable material, such as stainless steel. The housing 28 may be fluid tight and non-corrosive for operating in manufacturing environments. One end of the housing 28 may include a cap 30 for access to the interior of the housing and the elements disposed therein. The cap 30 may be removably threaded onto the housing 28 or otherwise secured thereto and may be fluid tight when secured.

The end of the housing 28 opposite the cap 30 includes an illuminating and viewing panel 32. The illuminating and viewing panel 32 includes one or more illumination ports 34 for permitting light or the like emitted from the emitter 24 to be directed outwardly from the housing. Illumination ports 34 include a material that transmits the particular source radiation out of the housing 28 and preferably exhibits strength and corrosion resistance. By way of example, illumination ports 34 can be made of borosilicate glasses, quartz glasses, acrylics, optical grade polymers, and similar transparent or translucent materials. Each illumination port 34 is individually fused at high temperature in position in the panel 32 to maintain a hermetic seal between the exterior of the housing 28 and the interior of the housing. The fusing process followed in the present invention is similar to that process described in *Glass Engineering Handbook, Third Edition,* Chapter 5, (1984) Library of Congress ISBN 0-07044823-X by G. W. McLellan and E. B. Shand. Illumination ports 34 may be plano-plano lenses; however, other lens configurations can be used depending upon the application. For example, if divergence of an illumination beam of source radiation is desired, the associated illumination port 34 can be a biconcave, plano concave, or negative meniscus lens. Conversely, if convergence of an illumination beam of source radiation is desired, the associated illumination port 34 can be a biconvex, planoconvex, or positive meniscus lens. Individual lenses may also be fitted with protective, laminated or unlaminated covers to guard against corrosion, fiber light and/or change lens optics on the internal side of the unit.

The illuminating and viewing panel 32 includes a view port 36 to permit light or the like to enter the housing 28 and be detected by the detector 22. View port 36 includes a material that transmits detectable radiation through the port and provides a seal to the housing 28. The detectable radiation can be the same as the source radiation or different from the source radiation, depending on the application. Accordingly, view port 36 can be manufactured from a material transmitting the entire spectral range of the source radiation for enabling detection of specular and diffuse reflections of source radiation by the interior contents of the vessel. As an alternative, view port 36 can be manufactured from a material, which filters out unwanted spectral regions from radiation to be detected, or which transmits only a chosen wavelength of light. For instance, if the source radiation is of a shorter wavelength intended for fluorescence excitation, and the detectable radiation of interest is a longer wavelength fluorescence, then view port 36 can be chosen to transmit only longer wavelengths of interest. Where observations are being performed by a user, visible light is generated and detected by detector 22 and conveyed to the user for making observations and/or a computer that performs analysis of the images and/or video captured.

It is noted that the particular arrangement of illumination ports 34 and view port 36 in the presently described embodiment is subject to change depending upon the specific application. For example, as few as one, or more than six, illumination ports 34 can be provided in any pattern of locations in panel 32. The view port 36 can be off-center (not axially aligned).

The housing 28 also includes a power input connection 40 for connecting elements of the device 20 to external electrical power and a signal/data connection 42 for connecting elements of the device to external data and signal collecting and generating devices, such as a controller or controllers and/or a computer (not shown).

The detector 22 in the exemplary embodiment described herein may be a black and white or color camera (e.g., with a CCD) that detects radiation (such as visible light) and transmits image signals to a remote monitor (not shown)

and/or computer and is supplied power by power input 40. Other types of detectors are contemplated. For purposes of the present disclosure, the term "detector" is intended to encompass, without limitation, any device used to sense radiated energy, including photosensitive elements and arrays responding to infra-red light, visible light, and ultra-violet light; ultrasound imaging devices; CCDs; and radar sensors. Numerous types of lens systems are part of or available for use with the detector 22 suitable for use in practicing the present disclosure, including but not limited to wide angle, narrow angle, zoom, telephoto, and phase contrast lens systems. The detector 22 may be configured to capture video or still images or both.

The monitoring device 20 may include a radiation guide to convey radiation from the view port 36 to the detector 22. For purposes of the present disclosure, the term "radiation guide" is intended to encompass, without limitation, any device used to constrain or guide radiation along a defined path without significant energy loss, including optical waveguides, light pipes, fiber optic bundles, and the like.

The emitter 24 may include one or more light emitting diode (LED) or other radiation-generating device as the source of radiation for the generation of light or the like and for the purpose of illuminating the area of interest or an observation zone. The term "illuminate" and "light" as used herein in its various forms, refers to application of radiation in any form, to a subject. Similarly, the term "detect" or "view," as used herein in its various forms, refers to detection of radiation generally, and is not limited to detection of light.

A built in thermal regulation system 46 is disposed in the housing, which maintains the temperature at view port 36 to be at least about 100° Fahrenheit (F), to reduce or prevent condensation formation. The temperature generated by the thermal regulation system 46 is set to maintain the view port 36 at an equal or greater than process temperature and above an ambient temperature of the environment surrounding the equipment in which the process is being conducted. The thermal regulation system 46 constructed based on the operating principle of a thermoelectric cooler. As energy (electricity) is applied across the thermal regulation system 46, the difference in metals making up each half of the circuit cause one junction of the circuit to cool down and the other to heat up. The cool side extracts heat from a surrounding area and the hot side dumps heat into its surrounding area.

The thermal regulation system 46 includes one or more thermoelectric devices 48 positioned inside the housing 28 of the device 20 to provide thermoelectric heat management to the monitoring device 20, such that heat is dumped into the front section 50 of the housing where it warms the view port 36 and prevents the view port from being obscured by vapors condensing thereon that are generated by the manufacturing process. The cool side of the thermal regulation system 46 withdraws heat from the back section 52 of the housing where the CCD and an optional power transformer 58 are located thereby keeping them cool for optimal operation. If the CCD is run off of, for example 24 VDC, a power transformer might be omitted. The thermal regulation system also has a voltage regulator 54 to control the thermal electric devices 48 to avoid overheating the view port 36 and other elements in the housing 28.

Thermoelectric management uses the Peltier effect to create a heat flux between the junctions of two different types of materials. A Peltier cooler, heater, or thermoelectric heat pump is a solid-state active heat pump, which transfers heat from one side of the device to the other, with consumption of electrical energy, depending on the direction of the current. Such an instrument is also called a Peltier device, Peltier heat pump, solid-state refrigerator, or thermoelectric cooler (TEC). Unlike typical applications of thermoelectric heat pumps, which use only heating or cooling, the instant application uses both heating and cooling to benefit operation of the device 20.

The monitoring device 20 of the disclosure is an integrated device that does not require a separate power supply enclosure as all elements are incorporated into one housing, and only electricity and a data conduit need to be supplied to the housing 28 to operate. The housing 28 may be minimal in size as space on and around a vessel with its limited space in a manufacturing environment. Integrating the detector 22, emitter 24, and power supply 58 all into one unit creates a small footprint on the vessel.

Image data detected by the detector 22 may be processed automatically using an optional image processor residing in a controller, which may be incorporated into the housing 28 or connected to remotely via Ethernet or any suitable communication system 42. The controller uses software to analyze the image for edge contrast to determine the level of liquid or foam and for change in illumination intensity, color or bubble size to detect and control foam. Another application of the controller is the quantification of foam. When using a process that foams, the user can use the monitoring device 20 of the disclosure to see when foam starts, the quantity of foam that occurs during the process, the color of the foam, and other aspects of the process. Previously, it has been challenging to analyze process with foam and processes that occur at high temperatures, as condensation tends to form on the viewing ports. Image based level monitoring also allows for a non-contact monitoring device which helps maintain sanitary needs in the industry.

The image based level monitoring outputs to a standard programmable logic controller (PLC) or digital command switch (DCS) or contact switch. The PLC or DCS, for example, allows for automation to be incorporated into the manufacturing process. When the process is automated, optimization based on quantified data rather than human judgment can improve efficiency and overall quality control.

The controller 60 computes analytical data associated with the images captured and transmitted by the detector 22 and may control pulse rate and intensity of the emitter 24, for example. In the illustrated embodiment, the control system 60 is housed with the power supply 58. However, it is also possible for the control system 60 to be consolidated into a single unit, or to be spread over additional modules that perform discrete tasks. The controller 60 may include software that resides on and is operated by a microcontroller/computer. The control system 60 preferably includes at least one electronic controller that operates in a logical fashion to perform operations, execute control algorithms, store and retrieve data and other desired operations. These controllers may include or access memory, secondary storage devices, processors, and any other components for running applications. The memory and secondary storage devices may be in the form of read-only memory (ROM) or random access memory (RAM) or integrated circuitry that is accessible by the controller. Various other circuits may be associated with the control system such as power supply circuitry, signal conditioning circuitry, driver circuitry, and other types of circuitry. The term "controller" is meant to be used in its broadest sense to include one or more controllers and/or microprocessors that may be associated with the control system and that may cooperate in controlling various functions and operations of the components of the monitoring device 20. The functionality of the controller 60 may be implemented in hardware and/or software without regard to the functionality.

In operation, the controller 60 receives image data from the detector 22 and uses algorithms to analyze the images for determining certain characteristics of the process, such as the presence of and the level of foam and/or fluid. As a result of analyzing the images, the controller 60 produces analytical data that includes at least foam level. Once the analytical data has been determined by the computational unit of the controller 60, the image data can be deleted or stored.

The controller 60 may be configured to automatically add anti-foam substances when predetermined conditions are met or exceeded or may be configured to generate an alert or several types of alerts depending upon the process conditions.

The monitoring device 20 as set out above may be used in connection with a number of manufacturing processes and in various configurations at least partly dependent upon constraints of the process involved. Some of these configurations are set out hereinbelow as exemplary embodiments of a monitoring system including one or more monitoring device 20.

Figure 7A:
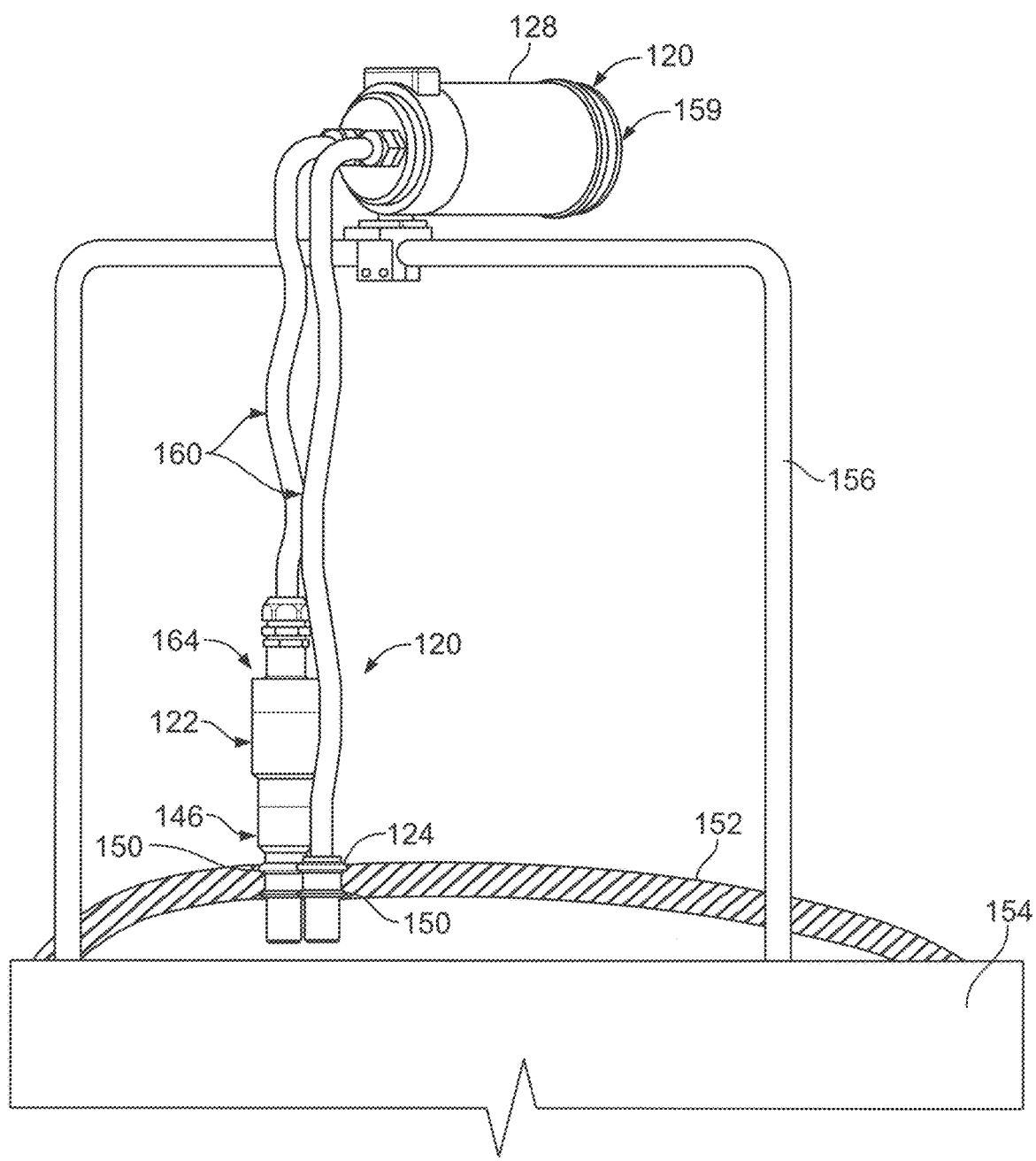
FIG. 7A is an embodiment of a monitoring device in a single-use setting with a first embodiment of a mounting system.

Turning to FIG. 7A another embodiment is disclosed of a monitoring device 120 that is similar to the previous devices with additional or adapted elements to apply to a "single-use" manufacturing environment.

Single-use refers to a pharmaceutical and biopharmaceutical industry term to identify sensitive processes where equipment cannot be reused and is disposed of In most cases, disposable plastic bags are employed inside of a vessel to maintain a high cleanliness level. The device 120, according to the present embodiment, is configured to mount to the single-use enclosure to perform process control monitoring functions while avoiding direct contact with the materials used in the process.

Single-use technologies are used in manufacturing for high cleanliness and R&D testing, for example. The device 120 of the present disclosure may be configured to be used in single-use applications. The monitoring device 120 is adaptable to different single-use products. For example, single-use technology may include 2,000 L disposable bags.

Figure 8:
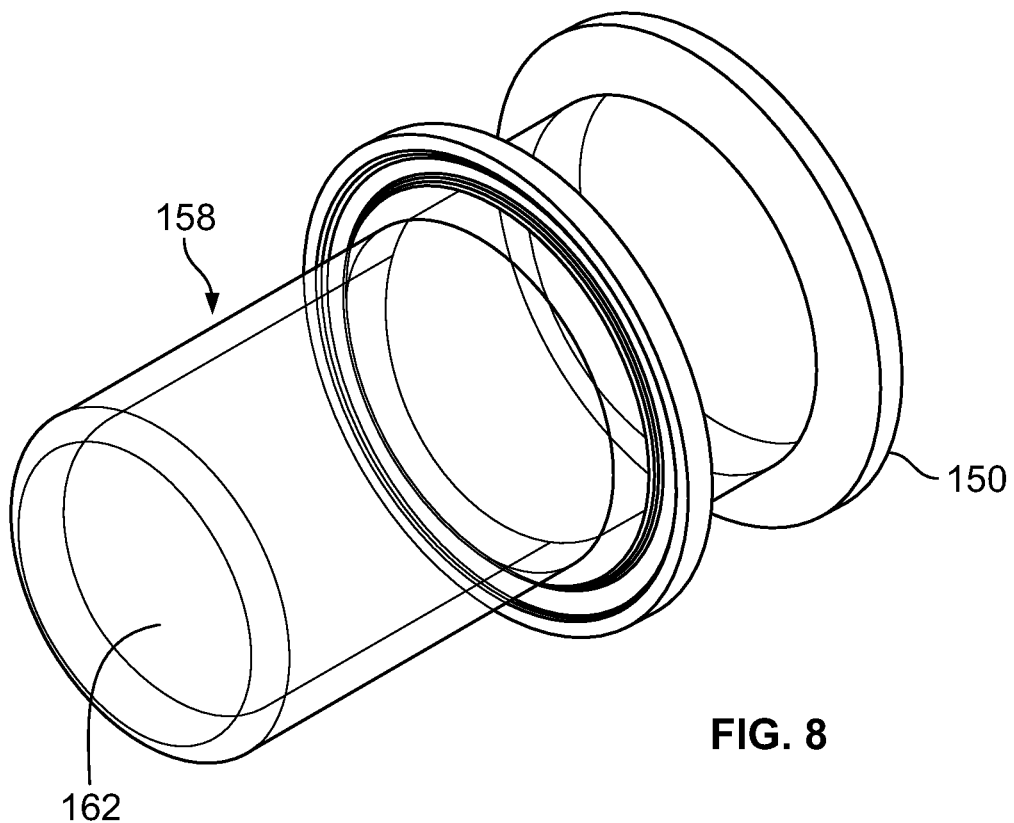
FIGS. 8-10 is a fitting for adapting a monitoring device according to embodiments of the disclosure in a single-use setting.
Figure 9:
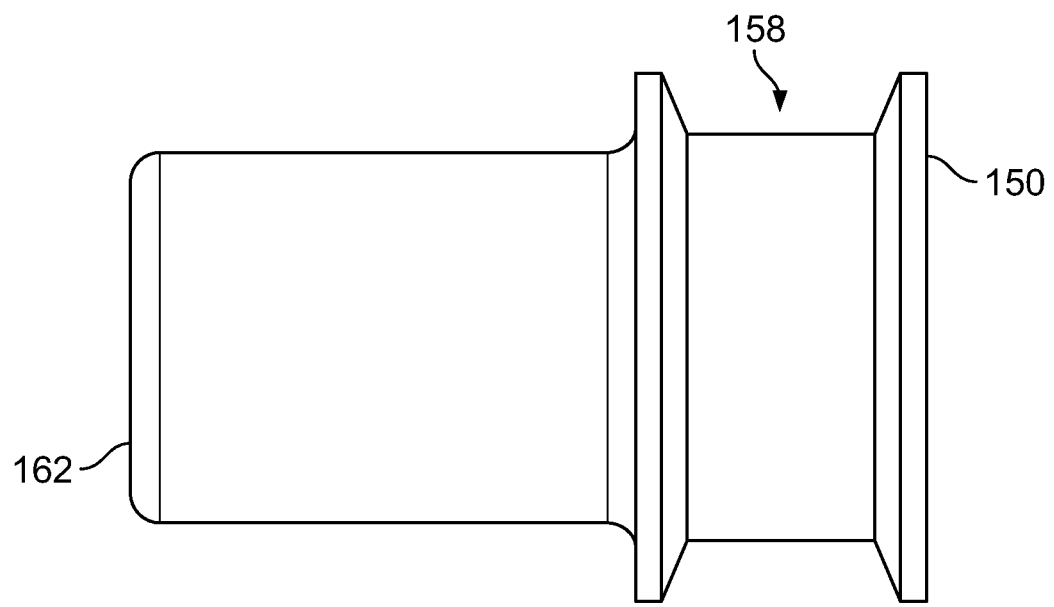
Figure 10:
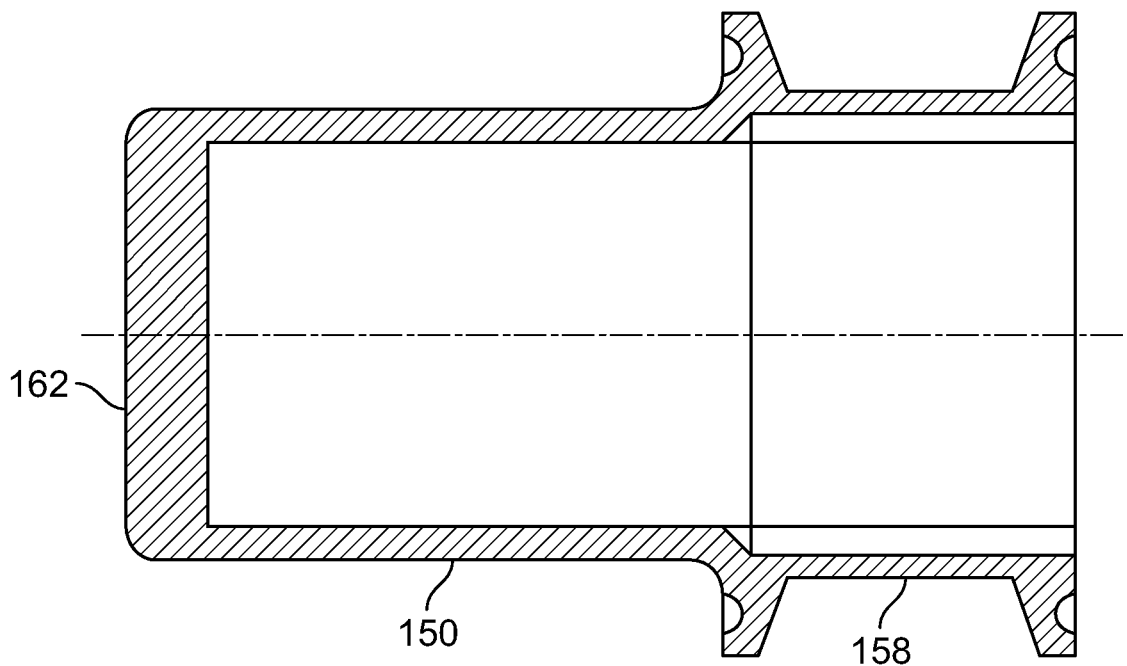

The monitoring device 120 is connectable to or includes an external fitting 150 (see also FIGS. 8-10) which mates to a plastic enclosure 152 made of Mylar, nylon or any suitable material with an acrylic, or other plastic, wall-fitting provided by the manufacturer of the enclosure 152. The enclosure 152 is sized and shaped to fit within a vessel 154. The fitting 150 maintains a seal with the enclosure 152 but can accept an externally disposed monitoring device 120 via the external fitting 150. The external fitting 150 holds detector 122, and/or emitter 124 of the monitoring device or other instrument as needed to monitor or control the process being performed in the enclosure 152. The enclosure 152 and fitting 150 would be used only once, and disposed at the end of the process. In the illustrated embodiment of 7A, the detector 122, and/or emitter, 124 of the monitoring device 120 are not contained within housing 128 and are connected to the housing via conduits 160 that supply power and data connectivity. The fitting 150 allows connectivity to the monitoring device 120 and allows inspection of the inside of the enclosure 152 without contamination of the internal ingredients or the device. Thus, the monitoring device 120 would be reusable.

The external fitting 150, returning to FIGS. 8-10 includes of a mating body 158 that is compatible with Tri-Clover sanitary clamps or other suitable clamps or connections. The fitting 150 is sized and shaped to hold and positions the detector 122 and/or emitter 124 near or in the wall of the enclosure 152. The detector 122 and/or emitter 124 may be separate—each connected to and held in place by a flexible conduit 160 that may have a memory or "stay put" feature. The conduit 160 allows positioning of the detector 122 and/or emitter 124 on the enclosure 152, prevents the weight of the detector 122 and/or emitter 124 from deforming the enclosure, and maintains a selected view angle. The "stay put" conduit 160 includes wiring or the like that connects to a power supply (see FIG. 7A) in the housing 128. The housing may be clamped onto the vessel 154, which holds the enclosure 152 in place or from a rod or rods 156 that can be adjusted in a 3-dimensional manner.

A thermal regulation system 146 is operatively associated with or disposed in the detector 122, which maintains the temperature at the front 162 or window portion of the fitting 150 of the glass, polycarbonate, or acrylic, for example, to be at least 100° F., reducing or preventing condensation forming as the front of the fitting is maintained at an equal or greater than process temperature. The thermoelectric devices of the thermal regulation system 146 are positioned inside the detector 122 such that heat thus generated is used to warm the fitting 150 and prevents condensation on the front 162 portion. The cool side withdraws heat from the back half 164 of the detector where a CCD is located thereby keeping the CCD cool for optimal operation. As in the above embodiment, a voltage regulator controls the thermal regulation system 146 to avoid overheating the fitting 150 and electronics in the detector 122.

The device 120 may include a controller 159 as in the above embodiment to analyze the level of foam or other properties of the fluids in the enclosure 152. The ability to quantify foam comes from image-based level detection, wherein the controller 159 distinguishes between foam and liquid. The ability to distinguish between foam and liquid allows the device 120 to quantify the amount of foam in the process, and when the foam starts. An optional automatic image analysis system can be incorporated into the controller 159 or connected to a remote computer-based computer system via Ethernet or an alternative communication protocol. The controller 159 analyzes the image for edge contrast to determine level of liquid or foam and for change in illumination intensity, and/or color of bubble size to detect foam and generate control signals to correct the level of foam. Another application the controller 159 may be configured to perform is the quantification of foam. In a process that generates foam, the user can use the detector 122 to detect and/or view when foam starts, the quantity of foam that occurs during the process, the color of the foam, and other characteristics thereof. Previously, it has been challenging to analyze a process with foam and processes with high temperatures, as it would cause condensation on the viewing ports. The image-based level monitoring provided by the devices and methods disclosed herein allows for non-contact monitoring which helps maintain sanitary needs in the industry.

The device 120 outputs data to a standard PLC or DCS or contact switch, for example. The PLC or DCS allows for automation to be incorporated into the manufacturing process. Automation incorporated into process allows for optimization based on quantified data rather than human judgment, which can be subjective.

Figure 7B:
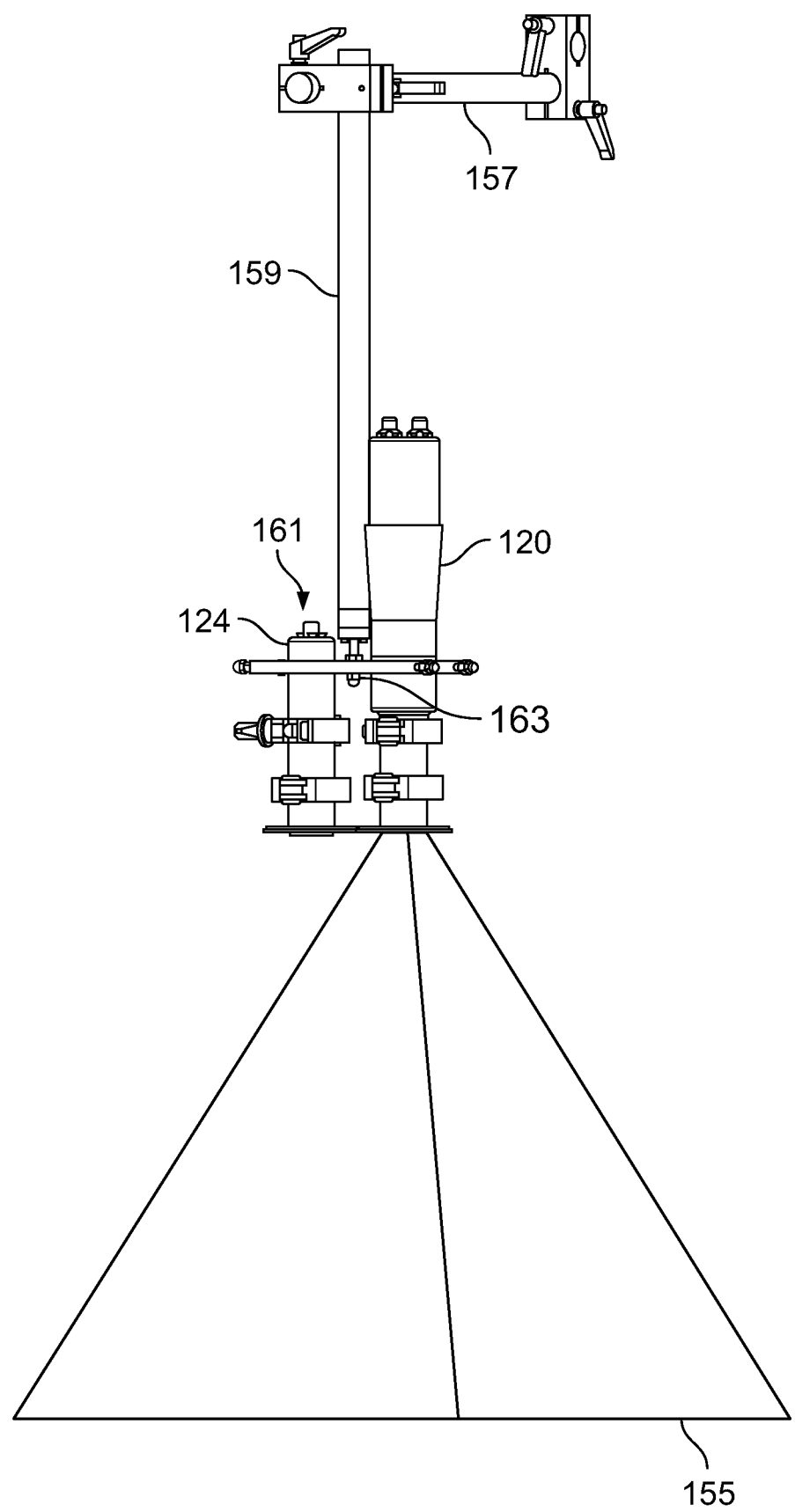
FIG. 7B-D is an embodiment of a monitoring device in a single-use setting with a second embodiment of a mounting system.
Figure 7D:
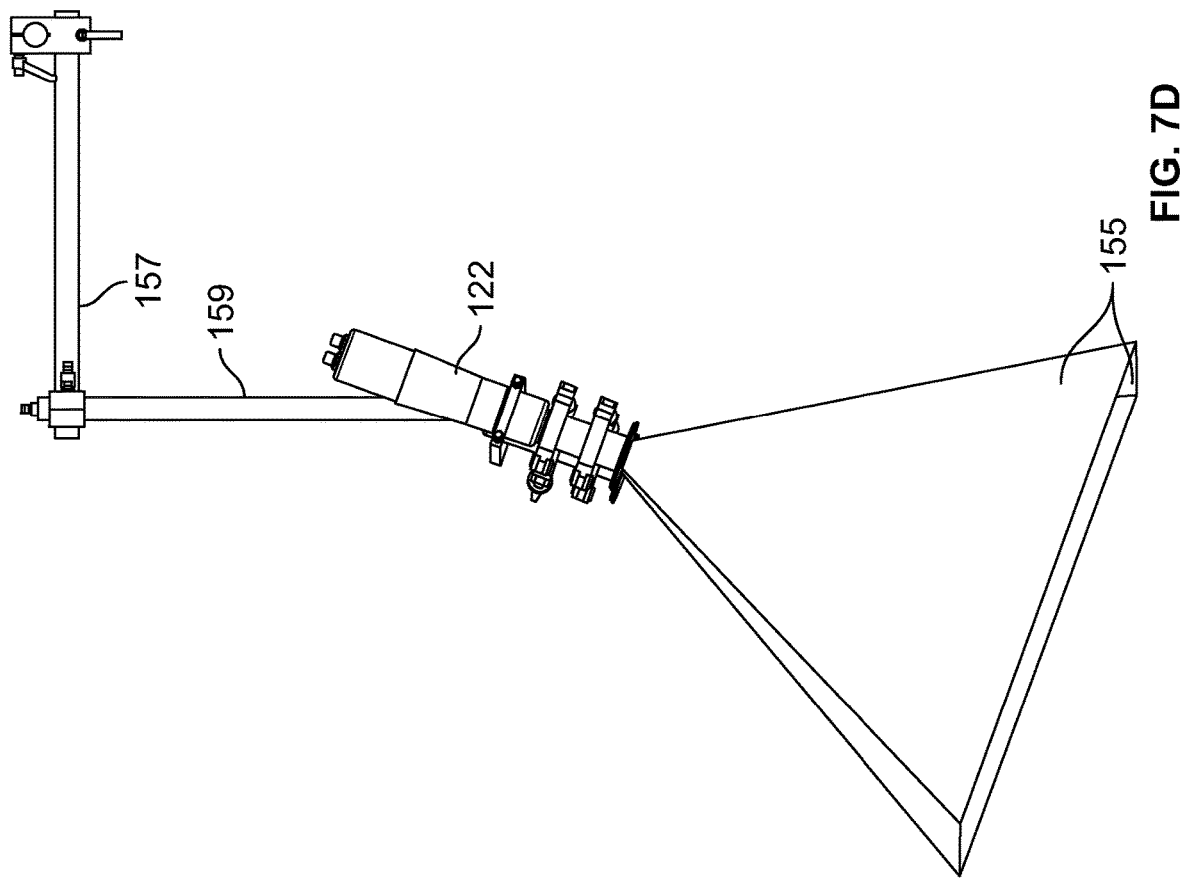
Figure 7C:
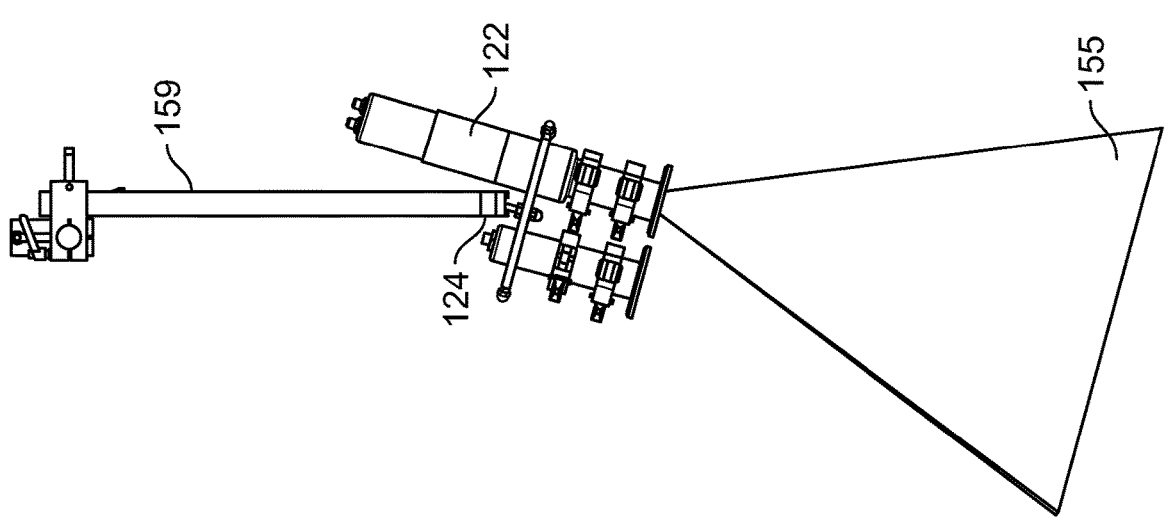

FIGS. 7B-D show an alternative mounting system 256 including a first rod 157 rotatably fixable in position. The first rod 157 may be disposed in a horizontal plane. A second rod 159 is rotatably fixable to the first rod 157. The second rod 159 may be disposed vertically. A distal end 161 of the second rod 159 includes a rotatable head 163 that permits variable orientation. The head 163 permits attachment of device 120 such that the device may be oriented in any direction.

Figure 11:
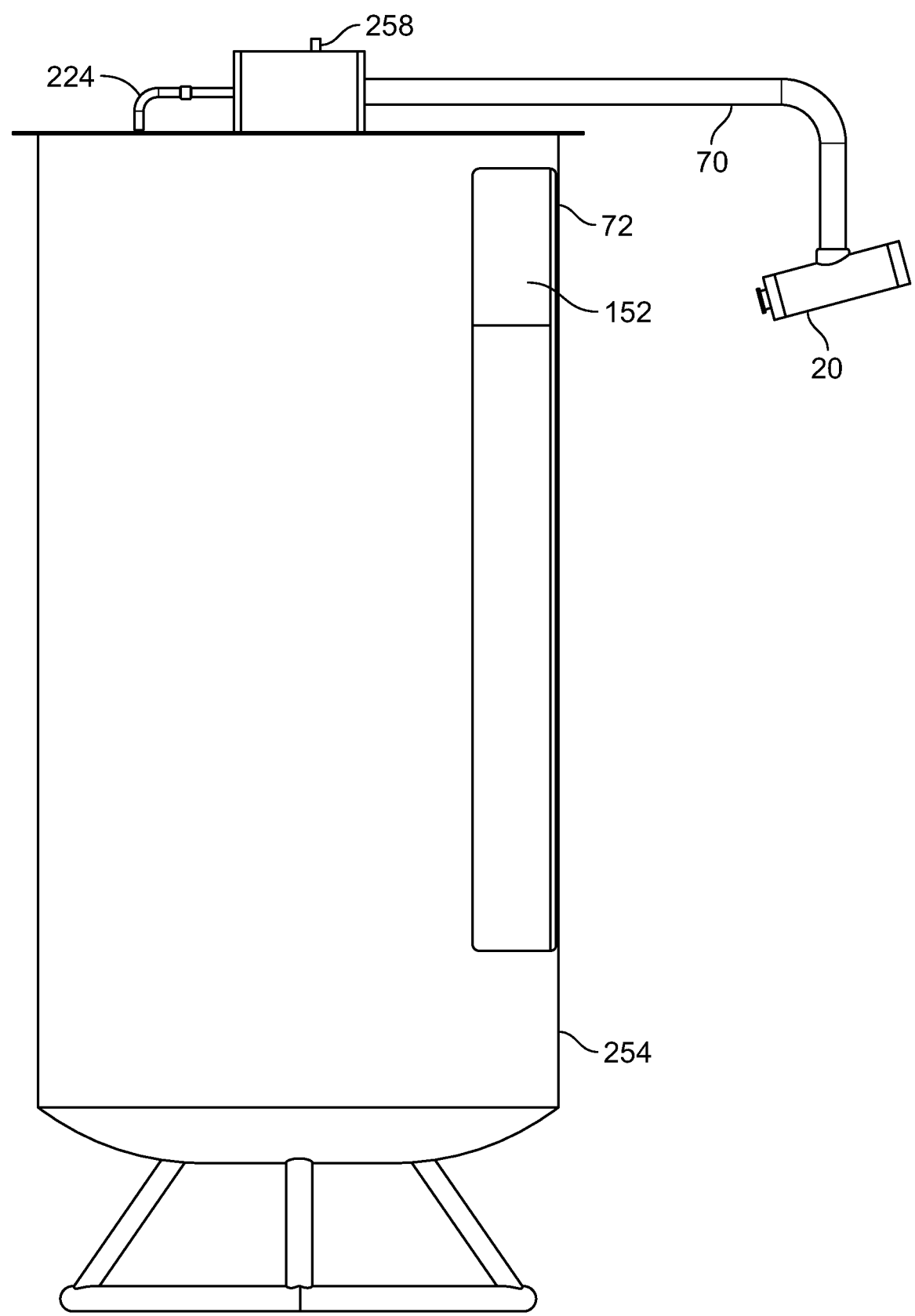
FIG. 11 is an embodiment of a monitoring device in a manufacturing setting and mounted exterior to a manufacturing vessel.

Referring to FIG. 11, the monitoring device 20 of FIG. 1 may be deployed in a manufacturing environment with an external mounting device 70 which positions the monitoring device so as to collect data through an external window 72 formed in the vessel 254. The monitoring device may include camera without a thermal regulating system because the monitoring device is spaced apart from the vessel 254. An enclosure 152 retains the materials used in the process inside the vessel 254 and the window 72 allows the monitoring device 20 to collect data through the material of the enclosure 152. The external mounting device 70 holds the monitoring device 20 and/or other instruments as needed to monitor and/or control the internal process. The window 152 and external mount 70 allows the user to visually inspect the interior of the vessel 254 and enclosure with the monitoring device 20 and illuminate the contents in the enclosure with an optional remote emitter 224 without the risk of contamination. The external mount 70 the monitoring device 20 and emitter 224 would be reusable.

The monitoring device 20 may include a separate power supply 258 that may be disposed, removably or permanently onto the vessel 254. In a single-use environment, the vessel 254 and/or power supply 258 may be configured to hold the enclosure 152 in the vessel or other structures may be provided, such as rods or the like, which are adjustable in a 3-dimensional manner.

Figure 12:
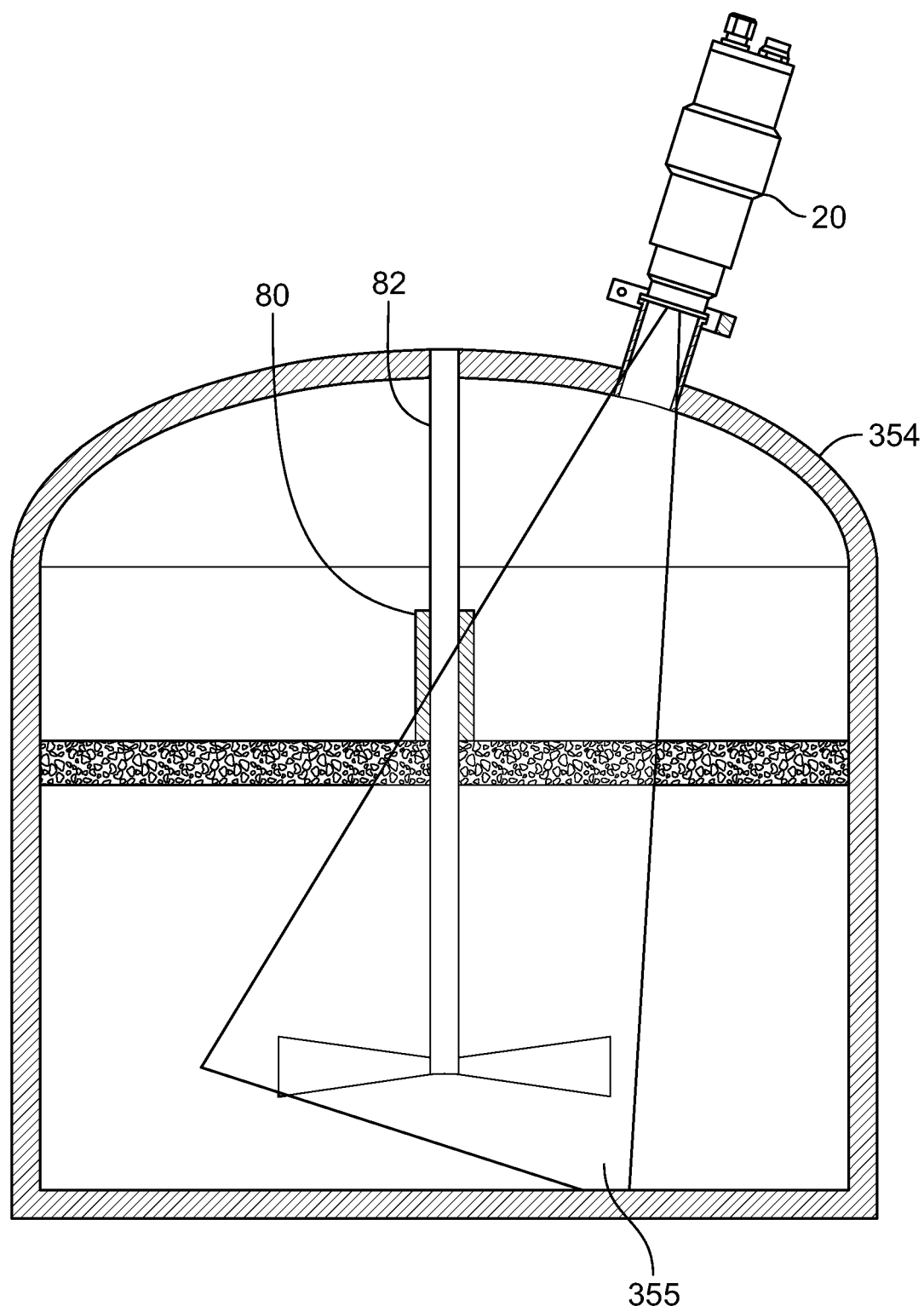
FIG. 12 is an embodiment of a monitoring device in a manufacturing setting and mounted directly to the manufacturing vessel.

Another embodiment of the disclosure is illustrated in FIG. 12, which combines a monitoring device 20, as set out in FIG. 1 or a conventional camera without a thermal regulation system, and a float 80 or such level detector on an agitator 82, baffle, or the like. The float-based level detector 80 rises and falls according to the level of foam and fluid in the vessel 354 due to its buoyancy. The monitoring device 20 and level detector 80 provides data to a process-based level monitoring system controller 60 disposed in the monitoring device or connected remotely. The monitoring device 20 and level detector 80 may be mounted in an optimum location on or near the top of the vessel 354 to improve the viewing capability of the system. The float 80 determines the exact height of the foam and fluid level. The monitoring device 20 provides viewing of the interior of the vessel 354 and imaging-based quantification and characterization of foam.

Figure 13:
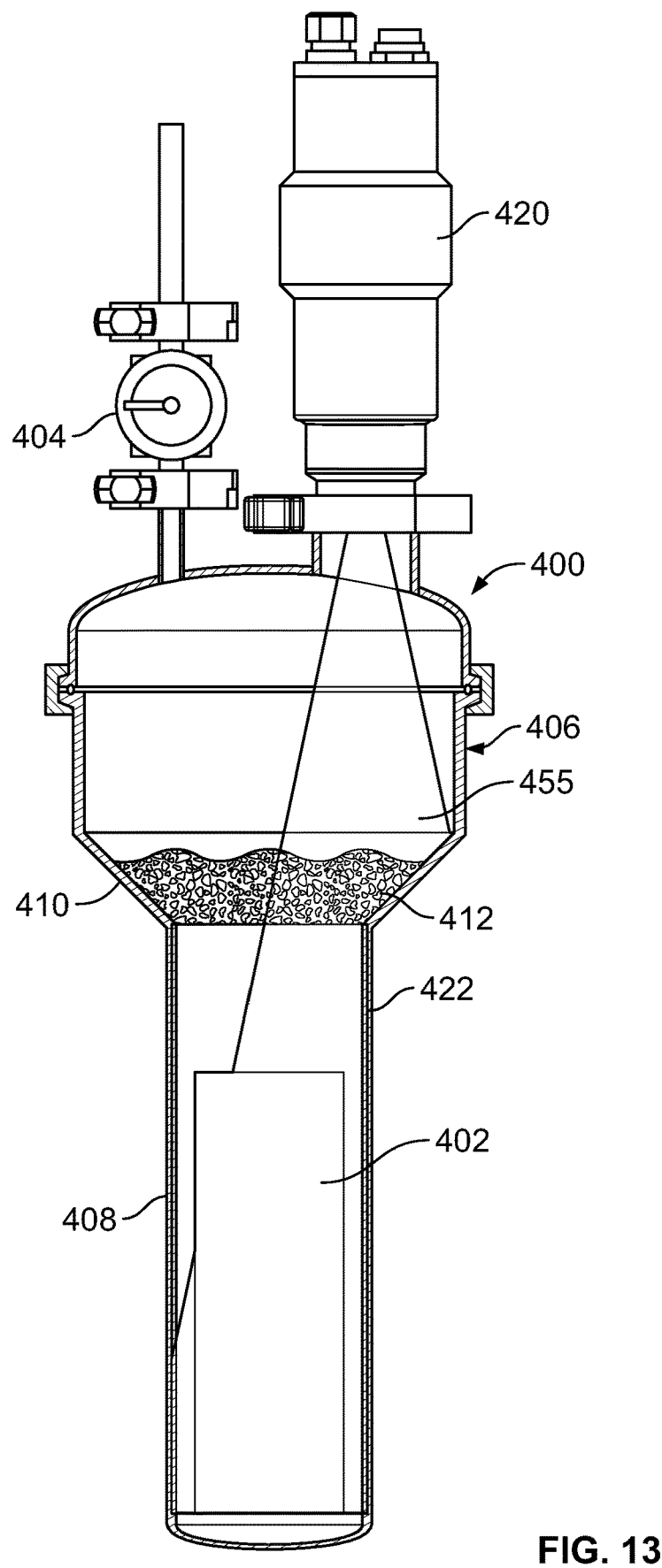
FIG. 13 is an embodiment of a monitoring device in a manufacturing setting and mounted directly to a bubble trap and filter system.

FIG. 13 shows a combined bubble trap and filter system 400, which may be used to provide improved chromatography performance while reducing chromatography skid footprint. The bubble trap and filter 400 may be applicable to chromatography operations performed in the biotech industry for the purification of biopharmaceuticals, nutraceuticals, specialty food ingredients and other biotechnology-derived products.

The technologies currently used in chromatography operations and found on most chromatography systems include a bubble trap and sub-micron pre-filter. Bubble traps are used to remove gases that could potentially come out of solution as the solution is presented to the chromatography resin bed. Entrained gas can potentially destroy the integrity of the chromatography bed. Gas bubbles interfere with the resin bed stationary phase by creating voids and pockets such that the mobile phase can bypass the resin matrix resulting in poor chromatography performance and potential loss of product.

Current bubble traps include a vessel of adequate volume to ensure that any gas entrained in the process solutions will be trapped prior to delivery to the chromatography resin bed. Some bubble traps are designed with an overflow feature that allows for release of gas while maintaining continuous flow of purged liquid to the chromatography column. A significant liquid reservoir is required that is mixed with the incoming buffer or load streams. The volume in the reservoir must be sufficient to mitigate the risk of entraining gas into the column while low enough to mitigate the risk of over-mixing and dilution of the process feed streams (ideally plug flow). In flow-through chromatography modes, large bubble trap volumes can result in diluted load volumes potentially resulting in reduced purification performance. The larger load volumes result in a wide and less distinct product chromatography peak with reduced separation efficiency. This is especially important in flow through chromatography systems. Poorly designed very large volume bubble traps may result in dead volume harboring lost product.

A well-designed bubble trap used in the manufacture of biopharmaceuticals should be designed for cleaning in place (CIP) and sanitization (thermal or chemical). Cleaning in place and sanitization of the chromatography pre-filter assembly is also critical for chromatography systems used in biopharmaceutical manufacturing. The ideal chromatography system used in the manufacture and purification of biopharmaceuticals is one that is cleanable by CIP and easily sanitized. It is also designed for optimal delivery of a load solutions that are free of gas and suspended solids that can interfere with the chromatography process and/or disturb the highly valuable chromatography resin bed.

FIG. 13 depicts a separate and distinct disclosure directed to a bubble trap system 400. The bubble trap system 400 may include a pre-filter 402 that removes suspended solids in the solutions presented to the chromatography system that could potentially foul the chromatography column and resin bed. The bubble trap 400 combines both a bubble trap and pre-filter 402 into a single optimal functioning device and further includes a monitoring device 420 as disclosed above.

The disclosed system 400 has been developed primarily for the biotechnology industry; however, the system is suitable for other applications and other industries. These include, but are not limited to chemical, petrochemical, food and other pharmaceutical applications as a few examples.

The bubble trap system 400 includes a pre-filter device 402 and a trap housing 422 including a code 7 filter mount (or multiple mounts) to accommodate a standard hydrophilic pre-filter (typically 0.45µ or 0.2µ or 0.1µ. Other filter types and sizes are contemplated. The bubble trap system 400 housing 422 is sized and shaped to accommodate the flow and capacity of the chromatography system with which it is designed to function. The housing 422 size is as small as possible to minimize dilution of the solutions (buffers and product load solutions) feeding the chromatography system and column. The housing 422 is configured adequately to allow for sufficient reaction time to remove entrained gas from feeds entering the chromatography system. The housing 422 is equipped with a rapidly responding/opening top port valve 404 designed to quickly and efficiently release gas from the feed solution prior to reaching the chromatography column.

The housing 422 includes an expanded section 406 connected to a base section 408 connected by way of a tapered 410 conical section, which provides for a minimal working volume that is far less than the working volume of a traditional, cylindrical bubble trap, and also reducing waste volume of a design incorporating a separate bubble trap and filter housing. The size and configuration of the bubble trap 400 will be understood to vary by application, as the rate of outgassing in the process is typically specific depending on the various applications and solutions at issue. Multiple configurations of geometry are therefore contemplated.

The monitoring device 420 in the system 400 is employed to generate signals that are used by a controller (see FIG. 1) to maintain a minimum liquid level 412 over the hydrophilic filter element 402. Loss of liquid level can result in the drying of the filter element 402 causing the filter element to block or bind, thus reducing filter capacity or function. Because of the small volume present in the housing 422, the monitoring device 420 is configured to supply a fast reaction time. The liquid level 412 may be maintained through automatic control of the valve 404 responsive to levels detected by monitoring device 420. The monitoring device 422 is configured to distinguish between foaming and gas bubbles, as foaming is a potential problem in chromatography operations.

The monitoring device 420 provides accurate imaging and thus a reading of liquid/foam level 412 and generates a signal output indicative of the presence and level of foam. The monitoring device 420 and associated elements are of a sanitary and hygienic design to promote and support efficient cleaning and sanitization of the chromatography system (not shown). Because the monitoring device 420 is of a non-contact construction enables the hygienic design. This is especially advantageous in biopharmaceutical applications. Other industries may also require special conditions such as explosion proof housings, high-pressure fittings or other features. The monitoring device may have other configurations in the same or similar bubble trap vessel geometry. As in the above embodiments, the monitoring device 420 may include a thermal regulation system to reduce the effects of condensation where the monitoring device interfaces optically with the housing 422. Alternatively, the monitoring device 420 omits a thermal regulation system.

In addition to the single element filter 402 illustrated; the filter may also use multiple filter element systems. The filter element 402 can be of any suitable design and configuration. The filter may be, but is not limited to polymer fiber, cloth woven fiber, pleated metal pore filters, coated and uncoated filters.

The monitoring device 420 may feed its output to a standard PLC, DCS, or contact switch. The PLC or DCS or other control system may be in communication with and operate an automated gas bleed valve 404 in the top of the housing 422 to control gas volume by venting or exhausting excess gas. The ability to continually and/or automatically exhaust or vent the gas above the liquid 412 allows the volume of gas in the bubbler trap system 400 to be a minimum volume for each process variation. The fluid level 412 in the filter bubbler can vary with each application and industry.

The monitoring device 420 operates to prevent liquid and/or foam from reaching the gas bleed valve 404. As gas is bled off, the fluid level 412 is likely to rise. In a housing configuration where the housing is not tapered, the level rise of liquid and foam can be more rapid than can be detected and acted upon. If a conventional level-detecting device is used with a straight walled filter canister, the change in level may faster than the control system can react to. In one contemplated configuration with a conical tapered expansion section 410 the monitoring device 420 can detect small changes in fluid level 412 and provides data for generating an adequate response via a control system (see FIG. 1).

Figure 14:
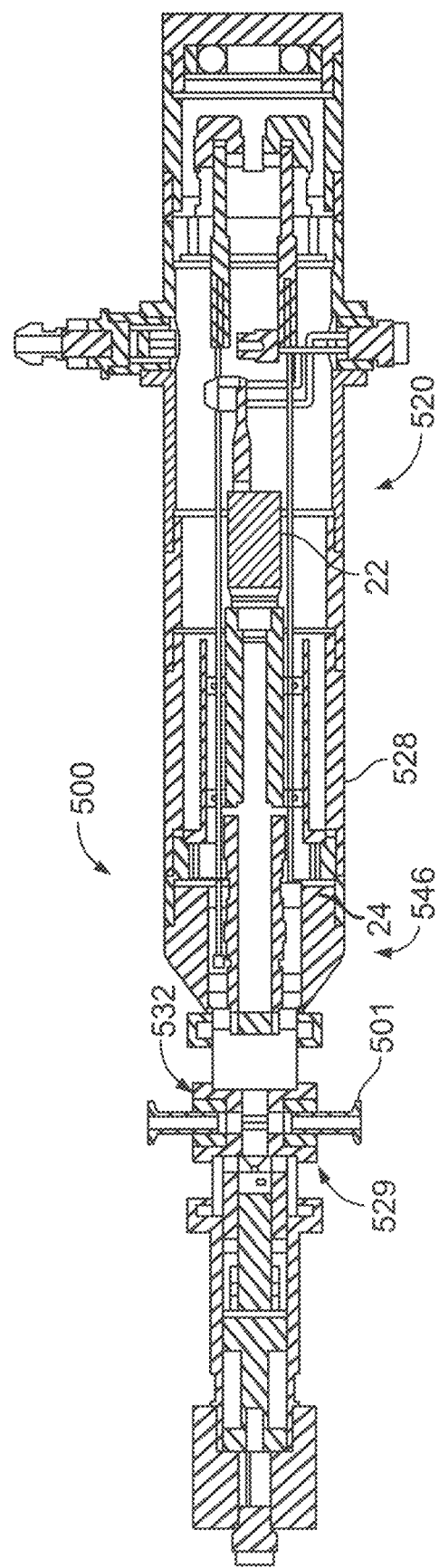
FIG. 14 is an embodiment of a monitoring device in a manufacturing setting and mounted exterior to a flow cell device in a single-use setting.

FIG. 14 shows a count monitoring system 500 for monitoring particle size, cell count, and the like without coming into direct contact with the process and in particular, suitable for use in a single-use setting as detailed above. Fluid flow cells are known. For example, a system 500 according to the present embodiment includes a fluid flow cell 501 as detailed in U.S. Pat. No. 6,771,366.

The flow cell portion of the system 500 includes a housing 529 defining an inlet and an outlet and a viewing assembly 532. The viewing assembly 532 provides an interface between the fluid flow cell 501 and a monitoring device 520, wherein the interface includes a plastic, e.g., Mylar, nylon, polycarbonate or acrylic, window or panel. The monitoring device 520 may be configured as in any suitable embodiments disclosed herein.

The interface 532 connects to a housing 528 of the device 520 with Tri Clover sanitary clamps, or any suitable connector, to secure the housing to the cell 501 and isolating the device 520 from the fluid flow through the cell. The housing 528 incorporates a detector 22 and emitter 24 as set out herein as well as an optional thermal regulation system 546. One application of the count monitoring system 500 is low concentration cell counting below without dilution $6 \times 10^6$ and with dilution $40 \times 10^6$ and higher concentrations. The system 500 can also be used for bubble detection in chromatography and cleanliness detection including applications to a single-use assembly to ensure that the strictest cleanliness level is maintained throughout.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A monitoring system for monitoring a process, comprising:
   a housing including a viewing panel, the viewing panel including a view port;
   an emitter configured to generate light and illuminate an observation zone of the process;
   a detector disposed within the housing, the detector configured to detect light entering the housing through the view port and create a plurality of images of the process in the observation zone; and
   a thermal regulation system configured to generate heat in the vicinity of the viewing panel of the housing so as to increase the temperature of at least the view port above ambient temperature,
   wherein the thermal regulation system is configured to heat a section of the housing comprising the viewing panel while simultaneously cooling another section of the housing opposite the viewing panel.

2. The monitoring system of claim 1, wherein the viewing panel includes at least one illumination port formed through the viewing panel.

3. The monitoring system of claim 2, including a plurality of illumination ports formed through the viewing panel.

4. The monitoring system of claim 2, wherein the at least one illumination port is provided with a light transmitting material.

5. The monitoring system of claim 4, wherein the light transmitting material is one or more of borosilicate glasses, quartz glasses, acrylics, and optical grade polymers.

6. The monitoring system of claim 2, wherein the emitter is disposed within the housing, and is configured to generate light through the at least one illumination port.

7. The monitoring system of claim 6, wherein the emitter is configured to generate visible light.

8. The monitoring system of claim 6, wherein the emitter includes at least one LED.

9. The monitoring system of claim 1, wherein the detector includes a photosensitive element.

10. The monitoring system of claim 1, wherein the detector is a CCD.

11. The monitoring system of claim 1, wherein the detector is configured to take and transmit one or both of still images and video.

12. The monitoring system of claim 1, wherein the thermal regulation system includes at least one thermoelectric device.

13. The monitoring system of claim 1, wherein the thermal regulation system heats the viewing port to at least about 100° F.

14. The monitoring system of claim 1, wherein the detector is disposed in the section of the housing opposite the viewing panel.

15. The monitoring system of claim 1, wherein the emitter is disposed in the section of the housing comprising the viewing panels.

16. The monitoring system of claim 1, further comprising a controller in communication with the detector and configured to receive and analyze data from the detector to determine one or more of a presence of foam in the observation zone, a level of foam in the observation zone, a rate of change of the level of foam in the observation zone, and the size and number of bubbles in the foam.

17. The monitoring system of claim 1, wherein the view port is one or more of borosilicate glasses, quartz glasses, acrylics, and optical grade polymers.

18. The monitoring system of claim 1, further comprising a power supply disposed within the housing.

19. The monitoring system of claim 18, wherein the housing comprises a first fitting for connecting the power supply to a source of power and a second fitting for connecting the detector to a data transmitting line.

20. The monitoring system of claim 1, wherein the housing is configured to be used in a single-use environment.

21. The monitoring system of claim 20, wherein the single-use environment includes a disposable enclosure and the housing is attachable directly to the enclosure.

22. The monitoring system of claim 21, further comprising a fitting that is attached to the enclosure and the housing.

23. The monitoring system of claim 21, further comprising a pair of fittings.

24. The monitoring system of claim 21, wherein the one of the pair of fitting is configured to receive the housing and the other of the fittings is configured to receive the emitter.

25. The monitoring system of claim 1, configured to attach to and monitor a flow cell.

26. A manufacturing system, comprising:
   a vessel sized and shaped for containing a manufacturing process; and
   a monitoring system for monitoring the manufacturing process, comprising:
      a housing configured to mount to the vessel, the housing including a viewing panel, the viewing panel including a view port;
      an emitter configured to generate light and illuminate an observation zone of the manufacturing process;
      a detector disposed within the housing, the detector configured to detect light entering the housing through the view port and create a plurality of images of the process in the observation zone; and
      a thermal regulation system configured to generate heat in the vicinity of the viewing panel of the housing so as to increase the temperature of at least the view port above ambient temperature,
      wherein the thermal regulation system is configured to heat a section of the housing comprising the viewing panel while simultaneously cooling another section of the housing opposite the viewing panel.

27. The manufacturing system of claim 26, wherein the monitoring system is attached directly to the vessel.

28. The manufacturing system of claim 26, wherein the monitoring system is attached to the vessel in a spaced apart configuration.

29. The manufacturing system of claim 28, wherein the monitoring system is attached to the vessel with a movable orientation.

30. The manufacturing system of claim 26, wherein the emitter and detector of the monitoring system are separately attached to the vessel.

31. The manufacturing system of claim 26, wherein the emitter and detector of the monitoring system are disposed within the housing.

32. The manufacturing system of claim 26, wherein the manufacturing process includes fermentation.

33. The manufacturing system of claim 26, further comprising a float disposed within the vessel and within the observation zone, wherein the detector is configured to monitor the position of the float and thereby generate data related to the position of the float and the level of a fluid within the vessel.

34. A single-use manufacturing system, comprising:
a vessel sized and shaped for containing a manufacturing process;
a single-use enclosure sized and shaped to fit within the vessel, wherein the single-use enclosure is a disposable plastic bag;
a fitting configured to attach to the single-use enclosure; and
a monitoring system for monitoring the manufacturing process, comprising:
   a housing including a viewing panel, the viewing panel including a view port, the housing configured to attach to the fitting;
   an emitter configured to generate light and illuminate an observation zone of the manufacturing process;
   a detector disposed within the housing, the detector configured to detect light entering the housing through the view port and create a plurality of images of the process in the observation zone; and
   a thermal regulation system configured to generate heat in the vicinity of the viewing panel of the housing so as to increase the temperature of at least the view port above ambient temperature,
   wherein the thermal regulation system is configured to heat a section of the housing comprising the viewing panel while simultaneously cooling another section of the housing opposite the viewing panel.

35. The manufacturing system of claim 34, wherein the emitter and detector of the monitoring system are separately attached to the single-use enclosure.

36. The manufacturing system of claim 34, wherein the emitter and detector of the monitoring system are disposed within the housing.

37. The manufacturing system of claim 34, wherein the manufacturing process includes fermentation.

38. The manufacturing system of claim 34, further comprising a float disposed within the enclosure and within the observation zone, wherein the detector is configured to monitor the position of the float and thereby generate data related to the position of the float and the level of a fluid within the enclosure.

\* \* \* \* \*